United States Patent [19]

Stillwell

[11] Patent Number: 4,457,307

[45] Date of Patent: Jul. 3, 1984

[54] BONE CUTTING DEVICE FOR TOTAL KNEE REPLACEMENT

[76] Inventor: William T. Stillwell, 96 S Long Beach Rd., Nissequogue, N.Y.

[21] Appl. No.: 409,920

[22] Filed: Aug. 20, 1982

[51] Int. Cl.³ .................................... A61B 17/14
[52] U.S. Cl. .............................. 128/317; 128/92 E; 128/92 EB; 128/305; 83/745
[58] Field of Search ............... 128/305, 317, 92 E, 128/92 EA, 92 EB; 30/166 A, 372, 379, 379.5, 371, 376; 83/743-746, 758, 761

[56] References Cited

U.S. PATENT DOCUMENTS 3,945,377  3/1976  Kronner ..................... 128/92 EB
4,008,720  2/1977  Brinckmann et al. ........... 128/317
4,349,018  9/1982  Chambers ..................... 128/92 E

FOREIGN PATENT DOCUMENTS 869842  7/1949  Fed. Rep. of Germany .... 128/92 E

Primary Examiner—C. Fred Rosenbaum
Assistant Examiner—Gene B. Kartchner
Attorney, Agent, or Firm—Finnegan, Henderson, Farabow, Garrett & Dunner

[57] ABSTRACT

A device for enabling a surgeon to make bone cuts in performing total knee surgery which includes a femoval assembly adapted to be mounted on a femur, and a carriage assembly connected to the femoval assembly and pivotally adjustable relative thereto about two axes which are transverse to each other and to the femoval axis. The carriage assembly is also adjustable longitudinally of the femoval assembly and includes a saw carriage slidable thereon. The saw carriage supports a powered saw. The parts are adjusted and locked in several sequential positions and the saw carriage and saw moved to make all the knee surgery cuts.

9 Claims, 13 Drawing Figures

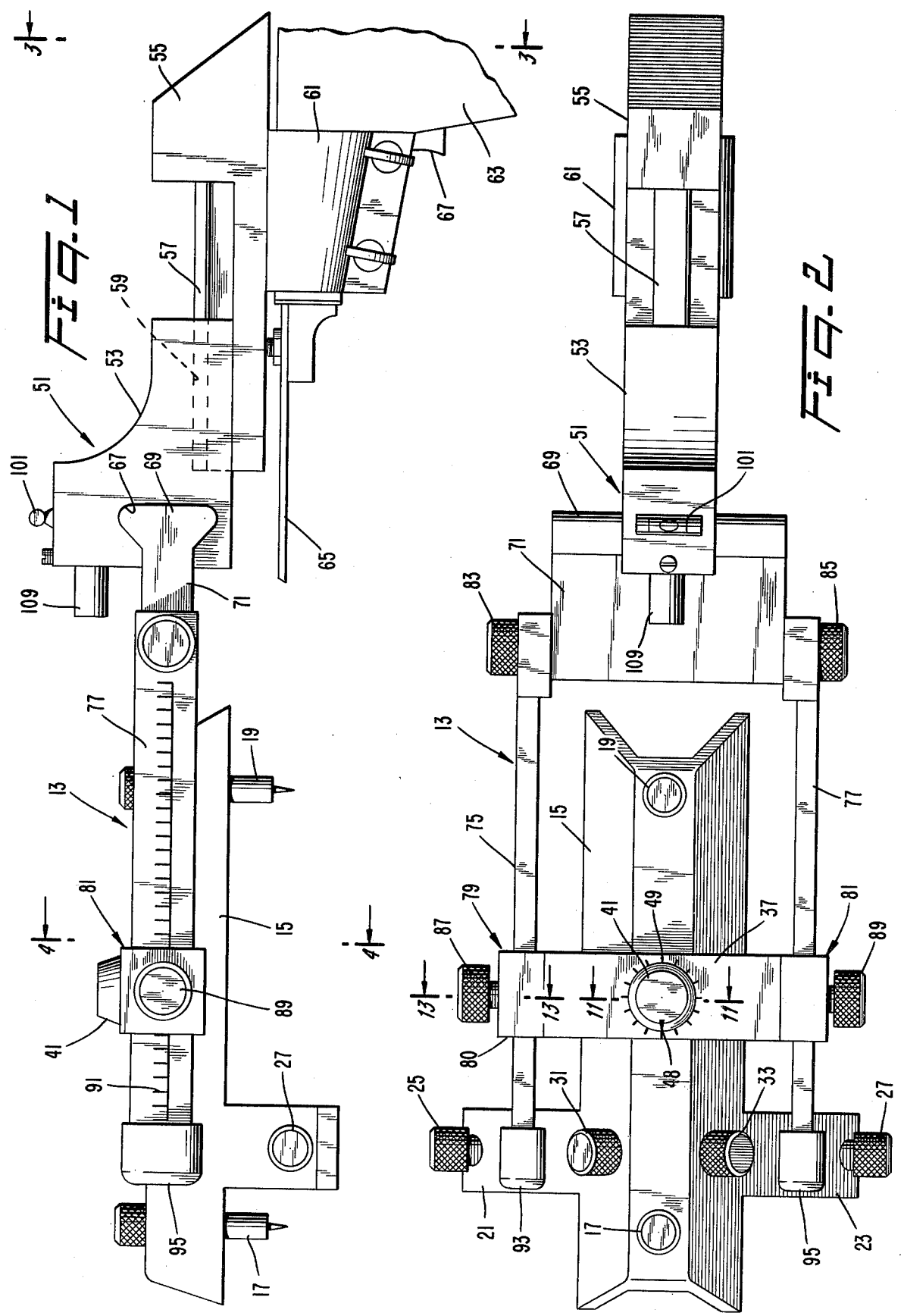

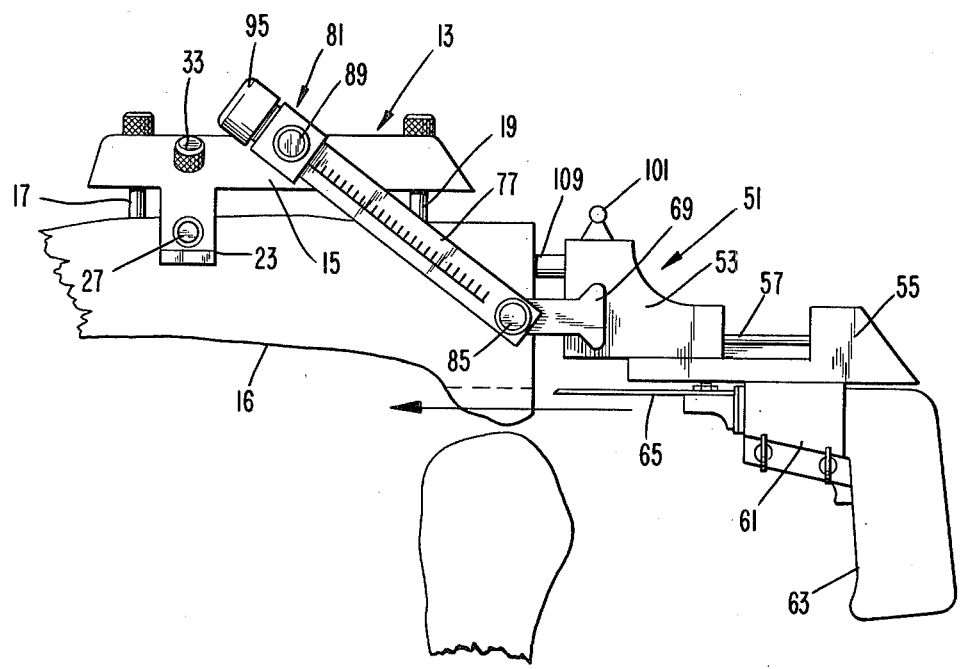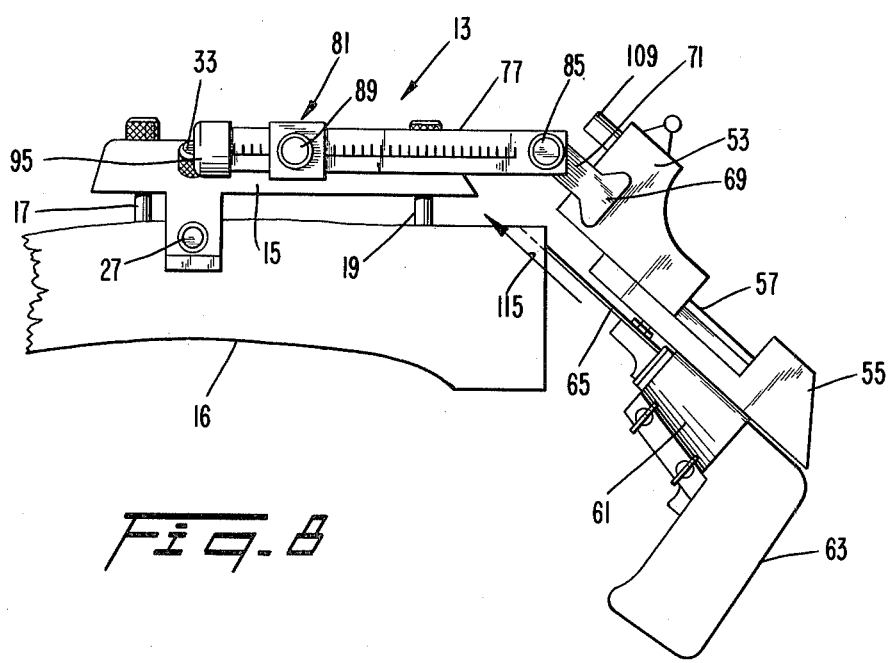

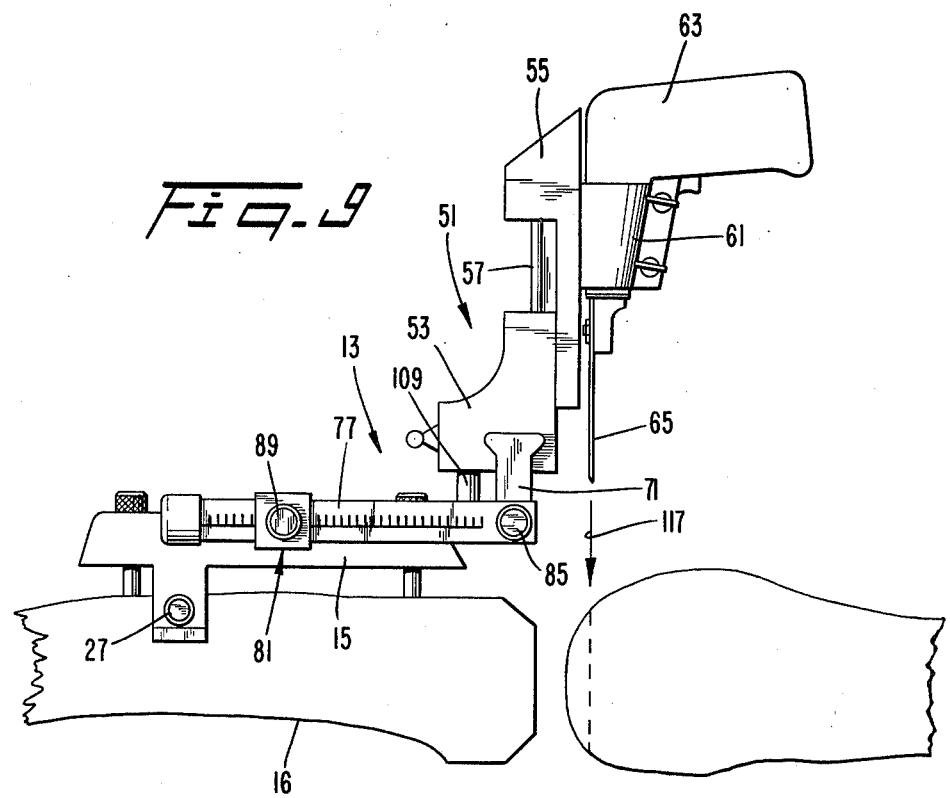
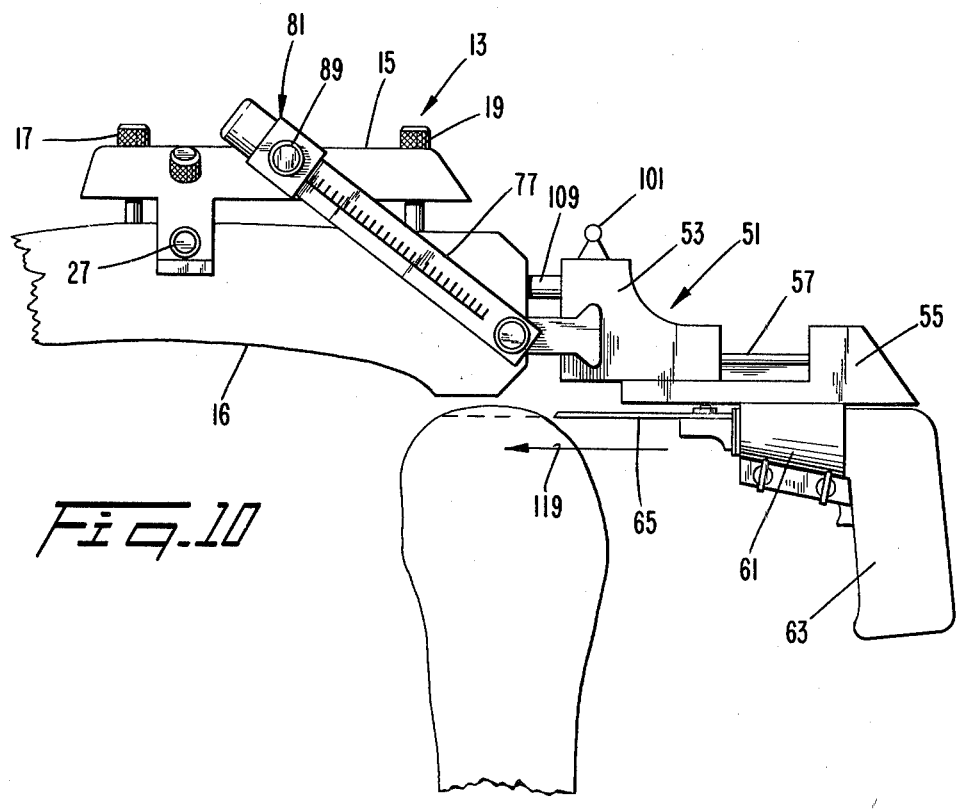

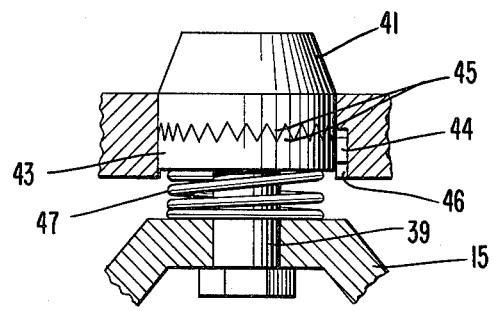
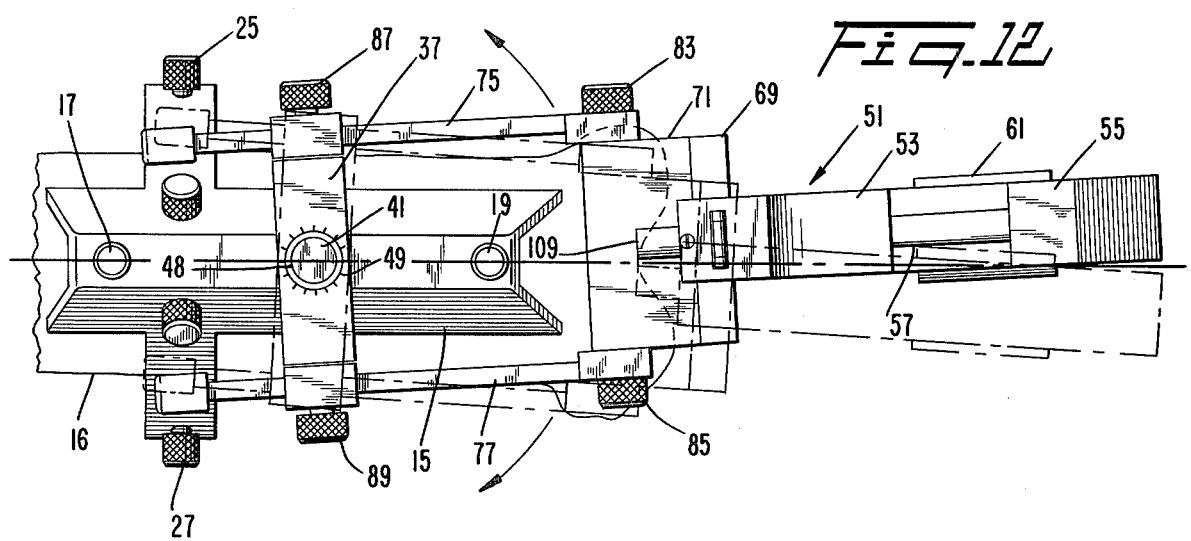
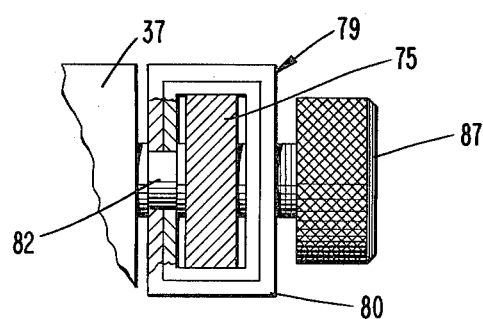

BONE CUTTING DEVICE FOR TOTAL KNEE REPLACEMENT

BACKGROUND OF THE INVENTION

The present invention relates to a device for use in making bone cuts during total knee replacement surgery, and more particularly to a device of this type which is adapted to be mounted in place on the patient's leg and enables the surgeon to make all the necessary bone cuts precisely and accurately.

Patients having severe knee damage arising, for example, from arthritis require surgery involving total knee replacement. In this surgery, multiple cuts are made on both the femur (thigh bone) and tibia (leg bone) and a knee replacement prothesis is installed to reproduce the function of the natural knee. The multiple bone cuts require considerable skill on the part of the surgeon in order to insure proper knee function. In addition to taking care not to damage surrounding ligaments, nerves, muscles, and vessels, the several cuts must be made accurately relative to the weight bearing axis of the leg. Otherwise, the repaired knee will not function properly.

To assist in this surgery, various guides, jigs, and templates have been proposed. While these are relatively successful in assisting the surgeon to make accurate cuts, they are often cumbersome and difficult to work with. Also, a large number of jigs or templates is required, often a different one for each of the several cuts to be made.

SUMMARY OF THE INVENTION

The present invention overcomes the problems and disadvantages of the prior art by providing a single device which assists the surgeon in making all the bone cuts required in total knee replacement. The device of the present invention mounts directly on the patient's leg, specifically the femur, and includes a moveable saw and saw carriage which are manually moved by the surgeon. The device is constructed so that relatively simple manual manipulations position the saw for each of the several cuts so that they can be made accurately and precisely.

Additional objects and advantages of the present invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and described herein, the device of the present invention comprises a femoral assembly including an elongated rail adapted to be secured to a femur and substantially parallel thereto, and a support pivotally mounted on the rail for movement about an axis substantially perpendicular thereto, a carriage assembly including a carriage housing and a saw carriage slidably guided for linear movement on the carriage housing, the saw carriage adapted to have a saw fixed thereto, the saw having a blade extending substantially parallel to the direction of linear movement of the carriage, means interconnecting the femoral assembly and the carriage assembly including adjustment means for securing the carriage assembly to the femoral assembly in several adjusted positions including a plurality of first positions where the saw carriage is slidably guided in substantially parallel paths which are substantially parallel to the elongated rail for making an anterior femur cut, a posterior femur cut, and a proximal tibia cut, a plurality of second positions where the saw carriage is slidably guided in substantially parallel paths which are substantially perpendicular to the elongated rail for making a transverse distal femur cut and for scoring the tibia cortex, and a plurality of third positions where the saw carriage is slidably guided in paths forming an acute angle with the elongated rail for making anterior and posterior femoral chamfer cuts.

Preferably, the invention includes a pair of spaced parallel arms pivotally secured to the support and to the carriage assembly for movement about first and second generally parallel axes, and the pivital connections between the arms and the support each includes means permitting adjustment of the arms longitudinally of the support. At least one of the arms is provided with indicia which assists the surgeon in determining the position of the saw blade relative to the elongated rail. Finally, the saw carriage is adjustable laterally relative to the femoral assembly and means is provided for establishing that the saw blade is in a true horizontal position.

The accompanying drawings, which are incorporated in and constitute a part of this specification, illustrate one embodiment of the invention and, together with the description, serve to explain the principles of the invention.

BRIEF DESCRIPTION OF THE DRAWINGS

FIG. 1 is a side elevational view showing a device constructed in accordance with the present invention;

FIG. 2 is a top plan view of the structure of FIG. 1;

FIG. 7 is a view similar to FIGS. 5 and 6 and showing the saw in position to make a posterior femur cut;

FIG. 8 is a view similar to FIGS. 5-7 and showing the saw in position to make an anterior chamfer cut;

FIG. 9 is a view similar to FIGS. 5-8 and showing the saw in position to make a transverse proximal tibia score;

FIG. 10 is a view similar to FIGS. 5-9 and showing the saw in position to make a transverse proximal tibia cut;

FIG. 11 is an enlarged sectional view of the structure of FIG. 2 taken along the line 11—11 thereof;

FIG. 12 is a view similar to FIG. 2 but to a reduced scale and showing the femur assembly mounted on a femur and the carriage assembly in adjusted positions relative to the femur assembly, in solid lines positioned substantially perpendicular to the weight bearing axis of the left femur; and FIG. 13 is an enlarged sectional view of the structure of FIG. 2 taken along the line 13—13 thereof.

DESCRIPTION OF THE PREFERRED EMBODIMENT

Figure 3:
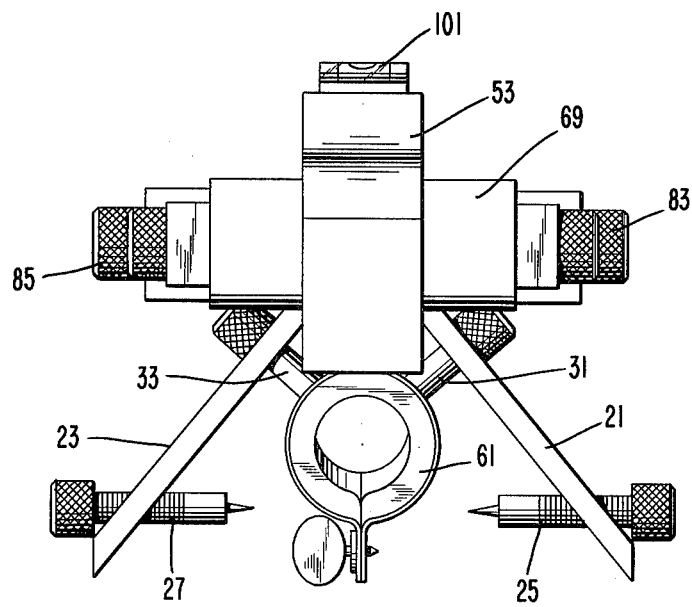
FIG. 3 is an end-view of the structure of FIG. 1 looking in the direction of the arrow 3—3.

Reference will now be made in detail to the present preferred embodiment of the invention, an example of which is illustrated in the accompanied drawings.

The preferred embodiment of the present invention is illustrated at 11 in FIGS. 1 and 2. In accordance with the invention, and as embodied herein, this device comprises a femoral assembly 13 which includes an elongated rail 15 adapted to be secured to a femur 16 (see also FIG. 5). The rail 15 has a plurality of femoral pins 17, 19 mounted thereon which have pointed ends adapted to penetrate the femur anterior and locate the rail substantially parallel to the femur. In addition, a pair of outriggers 21, 23 are formed near the proximate end of the rail 15 and each is provided with an outrigger pin 25, 27 respectively which are adapted to penetrate the femur at opposite sides (see also FIG. 4). Additionally, another pair of femoral pins 31, 33 may be provided, one on either side of the rail 15 adjacent the outriggers 21, 23. The pins 17, 19, 25, 27, 31, 33 cooperate to secure the rail 15 to the femur in substantial parallelity therewith.

Figure 4:
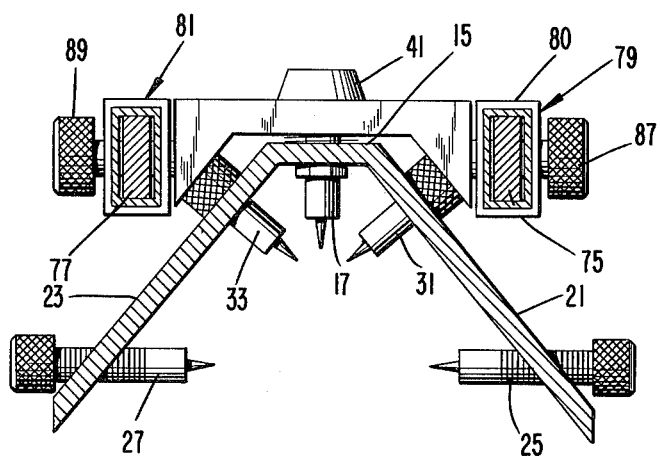
FIG. 4 is a sectional view of the structure of FIG. 1 taken along the line 4—4 and shown with the saw removed.

In accordance with the invention, the femoral assembly 13 includes a support which is pivotally secured to the elongated rail 15 about an axis substantially perpendicular thereto. As embodied herein and shown in FIGS. 2 and 11, a support 37 extends transversely of the rail 15 and is pivotally secured thereto by a bolt 39. As shown in FIG. 11, the bolt secures the rail 15 to an annular member 41 which is rotatably received in an opening 42 in the support 37. Another annular member 43 is slidably and non-rotatably received in the opening 42 by a cooperating key 44 and slot 46 on the member 43 and support 27, respectively. The members 41, 43 are formed with cooperating teeth 45. A compression spring 47 biases the members 41, 43 toward each other so that the cooperating teeth 45 normally prevent rotation of the support 37 relative to the rail 15. However, upon application of manual force to the support 37, the teeth 45 will ride up one another allowing the support 37 to be pivoted relative to the rail 15. As shown in FIGS. 2 and 4, the member 41 is provided with a pointer 48 which aligns with indicia 49 on the support 37 to indicate the angular position of the carriage assembly and saw blade relative to the femoral axis and the weight bearing axis as described below.

In accordance with the invention, a carriage assembly is provided which includes a carriage housing and a saw carriage slidably guided for linear movement on the carriage housing. The saw carriage is adapted to have a saw fixed thereto, the saw having a blade extending substantially parallel to the direction of linear movement of the saw carriage.

As embodied herein, a carriage assembly 51 includes a carriage housing 53 having a saw carriage 55 slidably supported thereon by a cooperating rail 57 and guides 59 (see FIGS. 1 and 2). Means (not shown) is provided on the saw carriage 55 and carriage housing 53 to limit travel of the saw carriage 55 relative to the carriage housing 53 in the right-hand direction as seen in FIG. 1. The saw housing 55 has a dependent socket 61 fixed thereto which is adapted to receive and to support the housing of a powdered saw 63 (see FIG. 5). The saw 63 includes a motor (not shown) which preferably is battery powered, and has a forwardly projecting blade 65. The saw 63 also includes a trigger 67 which, when depressed, actuates the motor and causes the blade 65 to oscillate about substantially a vertical axis which is perpendicular to the plane of the blade. As seen in FIG. 1, when the saw is positioned in the socket 61, the plane of the blade 65 is substantially parallel to the direction of linear movement of the saw carriage 55 as allowed by the rail 57 and guides 59 on the carriage 55 and housing 53, respectively.

In accordance with the invention, the saw carriage 55 is adjustable laterally relative to the femoral assembly 13. As embodied herein, the carriage housing 53 is provided with a transverse mortise 67 at its forward end which slidably receives a tenon 69 on a carriage track 71 (see FIG. 1). This allows the carriage housing 53 and saw carriage 55 and saw 63 to be adjusted laterally so that the lateral position of the saw blade 65 is also adjusted. A set screw 73 on the carriage housing 53 is tightened against the carriage track 71 to lock the carriage housing 53 in place.

In accordance with the invention, there is provided means interconnecting the femoral assembly 13 and the carriage assembly 51 which includes adjustment means for securing the carriage assembly to the femoral assembly in several adjusted positions. These include a plurality of first positions where the saw carriage 55 is slidably guided in substantially parallel paths which are substantially parallel to the elongated rail 15 for making an anterior femur cut, a posterior femur cut, and a proximal tibia cut; a plurality of second positions where the saw carriage 55 is slidably guided in substantially parallel paths which are substantially perpendicular to the elongated rail 15 for making a distal femoral cut and for scoring the tibia cortex; and a plurality of third positions where the saw carriage is slidably guided in paths forming an acute angle with the elongated rail 15 for making anterior and posterior femoral chamfer cuts.

As embodied herein, a pair of spaced parallel arms 75, 77 are pivotally secured to the support 37 by a pair of sleeve bearings 79, 81, and are pivotally secured to the carrriage track 71 by pivotal lock bolts 83, 85 so that the arms 75, 77 are pivotally secured to the support and the carriage assembly for movement about first and second generally parallel axes. The sleeve bearings 79, 81 are identical and, as shown in FIG. 13, the bearing 79 includes a rectangular sleeve 80 pivoted to the support 37 by a bearing 82. The arm 75 is slidably received in the sleeve 80 and is locked in place by a lock bolt 87 threaded into the sleeve 80 and tightened against the arm 75. The tightened bolt 87 also presses the arm 75 against the bearing 82.

When the bolts 87, 89 are loosened, the arms 75, 77 can be pivoted relative to the support 37 about an axis extending centrally through the bolts to raise and lower the carriage assembly 51 relative to the femoral assembly 13. Similarly, when the bolts 83, 85 are loosened, the carriage assembly 51 can be pivoted relative to the arms 75, 77 about an axis extending centrally through the bolts 83, 85. When the bolts 83, 85 and the bolts 87, 89 are tightened, the aforementioned pivotal movement is prevented.

In addition, when the bolts 87, 89 are loosened, the arms 75, 77 can be moved longitudinally of the support 37. At least one of the arms 75, 77 is provided with indicia 91 which aligns with the associated sleeve bearing 79, 81 whereby the vertical position of the sawblade 65 relative to the rail 15 can be determined in a manner hereinafter described. A pair of stops 93, 95 are provided on the arms 75, 77, respectively, to limit the extent of longitudinal movement of the arms relative to the support 37.

In use of the device of this invention to perform total knee replacement, the patient's femur is placed in a level socket. The femoval assembly 13 and the carriage assembly 51 are adjusted, after loosening the lock bolts 83, 85 and 87, 89, to position the arms 75, 77 and the carriage track 71 parallel to the rail 15. After making the necessary incisions in the knee area to expose the distal femur and proximal tibia, the femoral rail 15 is placed on the femur 16 and aligned substantially parallel therewith. The femoral pins 17, 19 are imbedded in the femur 16 and, after determining that the carriage assembly 51 is level by means of a bubble level 101, the femoral assembly 13 is secured to the femur 16 by imbedding the outrigger pins 25, 27, and the pins 31, 33 therein. The carriage assembly 51 is then adjusted by turning the support 37 about the axis of pin 47 so that the carriage assembly extends parallel to the weight bearing axis of patient's leg. The weight bearing axis extends along a line connecting the center of the hip, the center of the knee, and the center of the ankle and normally forms an angle of about 9 with the femoral axis which extends substantially centrally along the femur. This angle may vary for patients having hips which are wider or narrower than normal. The pointer 48 on the member 81 aligns with the indicis 41 on support 37 to accurately set the carriage assembly at the proper angle.

Figure 5:
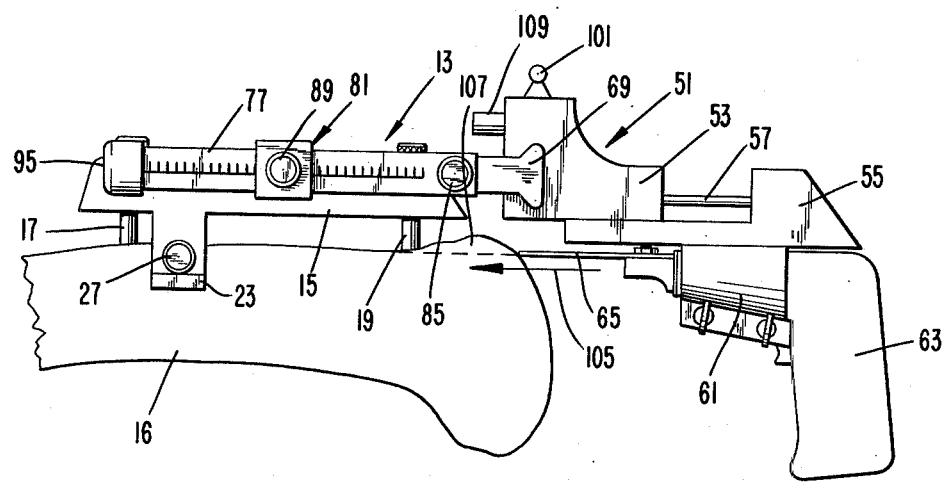
FIG. 5 is a view showing the device of the invention mounted and placed on a femur and with a saw in position to make an anterior femur cut.

The lock bolts 87, 89 are loosened and the carriage assembly 51 is adjusted (if necessary) by sliding the arms 75, 77 longitudinally of the sleeve bearings 79, 81 to position the saw blade 65 in confronting relation to the patient's knee with the saw carriage 55 withdrawn from the carriage housing 53 as shown in FIG. 5. (The posts are constructed so that when the carriage assembly is in this horizontal and level position, the saw blade 65 will be at the proper depth relative to the knee.) With the parts in the position shown in FIG. 5, the saw 63 is actuated by depressing the trigger 67 and the saw carriage 55 is moved back and forth in the direction of the arrow 105 to make an anterior femur cut. In this step, the saw blade 65 cuts and removes the femur trochlea 107.

Figure 6:
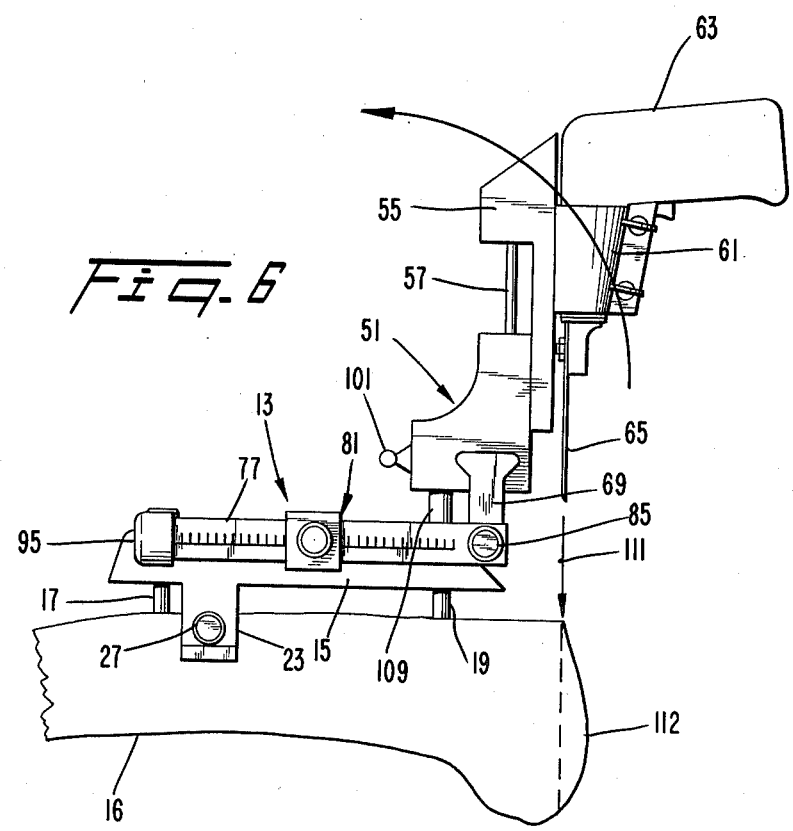
FIG. 6 is a view similar to FIG. 5 and showing the saw in position to make a transverse distal femur cut.

When this cut is completed, the bolts 83, 85 are loosened and the carriage assembly 51 is pivoted upwardly through 90° to now position the saw blade 65 perpendicular to the weight bearing axis of the leg as shown in FIG. 6. A stop pin 109 on the carriage housing 53 engages the femoral rail 15 to accurately locate the parts in this position. The saw 63 is again actuated and moved up and down to make a transverse distal femur cut in which it cuts the femur condyles 112. The pivot axis for the carriage assembly 51 defined by the bolts 83, 85 is positioned so that when the carriage assembly is pivoted upwardly through 90°, the saw blade is properly positioned relative to the knee to make the proper depth of cut on the femur condyles and that no adjustment of the arms 75, 77 is required.

Next, the parts are positioned as shown in FIG. 7. With the knee flexed, the locking bolts 83, 85 and 87, 89 are loosened so that the carriage assembly 51 can be lowered as shown. When the carriage 51 is leveled, the bolts are retightened. The arms 75, 77 extend along the hypotenuse of a right triangle formed by the plane of the blade 65, a vertical plane, and a plane passing through the arms 75, 77. Thus, a reading of the alignment of the sleeve bearing 81 with the scale 91 in this position of the parts when compared with the reading on the scale in the position of the parts shown in FIG. 5 can indicate to the surgeon the exact depth of the cut from the anterior condyles to the posterior condyles. With the parts in this position, the saw is again actuated and the saw carriage 55 moved back and forth in the direction of the arrow 113 to make a posterior femur cut in which the posterior condyles 114 are removed as shown.

Next, the parts are moved to the position shown in FIG. 8 to make an anterior chamfer cut. From the position shown in FIG. 7, the locking bolts 87, 89 are loosened, the arms 75, 77 repositioned parallel to the rail 15, and the bolts 87, 89 retightened. The bolts 83, 85 are loosened, the carriage assembly 51 is pivoted downwardly through an angle of about 45°, and the bolts 83, 85 retightened. Some small adjustment of the arms 75, 77 relative to the bearings 79, 81 may also be required. The saw 63 is again actuated and the saw carriage 55 moved back and forth along the direction of arrow 115 to make the anterior chamfer cut. When this is completed, the bolts 83, 85 are loosened, the carriage assembly 51 swung upwardly through an angle of 90°, the bolts 83, 85 retightened, and the saw 63 actuated and the carriage 55 moved back and forth along a line substantially perpendicular to the arrow 115 to make the posterior chamfer cut.

The knee is then extended, as shown in FIG. 9, and with the arms 75, 77 positioned parallel to the rail 15, the carriage assembly 51 swung to a vertical position where the stop pin 109 engages the rail and the bolts 83, 85 are retightened. With the arms 75, 77, extended to align the blade 65 with the proximal tibia as shown, the bolts 87, 89 are tightened. A spreader device (not shown) is used to tension and balance the ligaments in the leg. The saw 63 is actuated and the carriage 55 moved in the direction of arrow 117 to score the proximal tibia cortex. A complete cut is not made at this stage to avoid damage to popliteal vessels and nerves in the leg.

The proximal tibia cut is completed with the parts in the position shown in FIG. 10. In this position, the knee is flexed and the carriage assembly 51 moved to position the blade 65 in alignment with the previously made score. The arms 75, 77 are extended as shown and the bolts, 83, 85 and 87, 89 are tightened after the carriage assembly in leveled. The saw 63 is then actuated and the carriage 55 moved back and forth along the direction of arrow 119 to complete the tibia cortex cut. When this cut is completed, the device is removed from the patient's leg.

By the foregoing, there has been described a device for enabling a surgeon to make bone cuts in performing total knee replacement which greatly simplifies this operation and makes it significantly easier for the surgeon to successfully perform this surgery. It will be apparent to those skilled in the art that various additions, substitutions, modifications and omissions can be made to this device without departing from the scope or spirit of the invention. Thus, it is intended that the present invention cover the additions, substitutions, modifications and omissions provided they come within the scope of the appended claims and their equivalents.

What is claimed is:

1. A device for enabling a surgeon to make bone cuts in performing total knee replacement, said device comprising a femoral assembly including an elongated rail adapted to be secured to a femur and substantially parallel thereto, and a support pivotally mounted on said rail for movement about an axis substantially perpendicular thereto and to the femur, a carriage assembly including a carriage housing and a saw carriage slidably guided for linear movement on said carriage housing, said saw carriage adapted to have a saw fixed thereto, said saw having a blade extending substantially parallel to the direction of said linear movement of said carriage, means interconnecting said femoral assembly and said carriage assembly including adjustment means for securing the carriage assembly to said femoral assembly in several adjusted positions including a plurality of first positions where said saw carriage is slidably guided in substantially parallel paths which are substantially parallel to said elongated rail for making an anterior femur cut, a posterior femur cut, and a proximal tibia cut, a plurality of second positions where said saw carriage is slidably guided in substantially parallel paths which are substantially perpendicular to said elongated rail for making a transverse distal femur cut and for scoring the tibia cortex, and a plurality of third positions where said saw carriage is slidably guided in paths forming an acute angle with said elongated rail for making anterior and posterior femoral chamfer cuts.

2. A device as claimed in claim 1, said interconnecting means including a pair of spaced, parallel arms pivotally secured to said support and to said carriage assembly for movement about first and second generally parallel axes.

3. A device as claimed in claim 2, the pivotal connections between said arms and said support each including means permitting adjustment of said arms longitudinally relative to said support.

4. A device as claimed in claim 1, said saw carriage being adjustable laterally relative to said femoral assembly.

5. A device as claimed in claim 1, including means for establishing that the saw blade is horizontal.

6. A device as claimed in claim 3, at least one of said arms being provided with indicia to indicate the position of said saw blade relative to said elongated rail.

7. A devce as claimed in claim 1, said support and rail including indicia means indicating the angle formed between said rail and the direction of linear movement of said saw carriage.

8. A device as claimed in claim 1, including means releasably locking said rail and said support, and said carriage assembly to said femoral assembly.

9. A device as claimed in claim 2, the pivotal interconnections between said arms and said carriage assembly being dimensioned relative to the position of the saw blade so that upon completion of said anterior femur cut, said carriage assembly can be pivoted substantially 90° relative to said arms about said second axis to position said saw blade to make said transverse distal femur cut.

* * * * *